(12) United States Patent
Gao et al.

(10) Patent No.: US 11,974,590 B2
(45) Date of Patent: May 7, 2024

(54) METHOD OF FERMENTATION OF FISH PASTE BY MEDIUM HALOPHILIC BACTERIA

(71) Applicant: Jiangsu University, Jiangsu (CN)

(72) Inventors: Ruichang Gao, Jiangsu (CN); Zhiying Zheng, Jiangsu (CN); Li Yuan, Jiangsu (CN); Xiaoyun Wu, Jiangsu (CN); Qiaozhen Zhou, Jiangsu (CN); Qian Chu, Jiangsu (CN)

(73) Assignee: Jiangsu University, Jiangsu (CN)

( * ) Notice: Subject to any disclaimer, the term of this patent is extended or adjusted under 35 U.S.C. 154(b) by 1042 days.

(21) Appl. No.: 16/761,132

(22) PCT Filed: Mar. 29, 2019

(86) PCT No.: PCT/CN2019/080282
§ 371 (c)(1),
(2) Date: May 1, 2020

(87) PCT Pub. No.: WO2020/107760
PCT Pub. Date: Jun. 4, 2020

(65) Prior Publication Data
US 2021/0137143 A1 May 13, 2021

(30) Foreign Application Priority Data

Nov. 30, 2018 (CN) .......................... 201811451711.5
Nov. 30, 2018 (CN) .......................... 201811452816.2
Nov. 30, 2018 (CN) .......................... 201811452967.8
Nov. 30, 2018 (CN) .......................... 201811453568.3

(51) Int. Cl.

| | | |
|---|---|---|
| A23L 17/00 | (2016.01) | |
| A23B 4/005 | (2006.01) | |
| A23B 4/01 | (2006.01) | |
| A23B 4/02 | (2006.01) | |
| A23B 4/12 | (2006.01) | |
| A23L 3/10 | (2006.01) | |
| A23L 5/10 | (2016.01) | |
| A23L 27/24 | (2016.01) | |
| A23L 33/135 | (2016.01) | |
| C12N 1/20 | (2006.01) | |
| C12P 1/04 | (2006.01) | |
| C12R 1/07 | (2006.01) | |

(52) U.S. Cl.
CPC .............. *A23L 17/65* (2016.08); *A23B 4/005* (2013.01); *A23B 4/012* (2013.01); *A23B 4/02* (2013.01); *A23B 4/12* (2013.01); *A23L 3/10* (2013.01); *A23L 5/13* (2016.08); *A23L 17/70* (2016.08); *A23L 27/24* (2016.08); *A23L 33/135* (2016.08); *C12N 1/20* (2013.01); *C12N 1/205* (2021.05); *C12P 1/04* (2013.01); *A23V 2002/00* (2013.01); *C12R 2001/07* (2021.05)

(58) Field of Classification Search
CPC .......... A23L 17/65; A23L 17/70; A23L 27/24; A23L 3/10; A23L 5/13; A23L 33/135; C12N 1/20; C12N 1/205; A23B 4/012; A23B 4/02; A23B 4/12; C12P 1/04; C12R 2001/07; A23V 2002/00
See application file for complete search history.

(56) References Cited

U.S. PATENT DOCUMENTS

2021/0074384 A1* 3/2021 Apte ...................... G16H 20/60
2023/0263859 A1* 8/2023 Delisle ................... A61K 47/02
514/20.8

FOREIGN PATENT DOCUMENTS

| CN | 103740605 A | 4/2014 |
|---|---|---|
| CN | 103966146 A | 8/2014 |
| CN | 106085925 A | 11/2016 |
| CN | 108865954 | * 11/2018 |
| JP | H02-156895 A | 6/1990 |

OTHER PUBLICATIONS

Yoon et al. International Journal of Systematic and Evolutionary Microbiology (2003) vol. 53, pp. 1297-1303.*
Yoon et al. International Journal of Systematic and Evolutionary Microbiology (2004), vol. 54, pp. 803-808.*
Sun-Young An et al. International Journal of Systematic and Evolutionary Microbiology (2007), vol. 57, pp. 2476-2479.*
English Translation for CN108865954 published Nov. 2018.*

* cited by examiner

*Primary Examiner* — Anthony J Weier
(74) *Attorney, Agent, or Firm* — Fitch, Even, Tabin & Flannery, LLP

(57) ABSTRACT

The patent discloses halophilic bacteria and a method for fermenting fish paste, belonging to the technical field of solid-state fermentation of aquatic products using microorganisms. Four kinds of screened halophilic bacteria were used as mixed starter culture to produce fish paste. The effects of the ratio of mixed starter culture, inoculation amount, fermentation temperature, fermentation time and salinity on fish paste were studied by determining physical and chemical indexes and performing sensory evaluation. The fish paste has the characteristics of high safety, low salinity, high flavor and nutrition value. This method of fish paste processing needs short fermentation time. The fermented products of fish paste with better flavor can be obtained by using the mixed starter culture.

4 Claims, 3 Drawing Sheets

METHOD OF FERMENTATION OF FISH PASTE BY MEDIUM HALOPHILIC BACTERIA

CROSS-REFERENCE TO RELATED APPLICATIONS

This application is a U.S. national phase application filed under 35 U.S.C. § 371 of International Application Number PCT/CN2019/080282, filed Mar. 29, 2019, designating the United States, which claims priority from Chinese Application Number 201811452967.8, filed Nov. 30, 2018, Chinese Application Number 201811451711.5, filed Nov. 30, 2018, Chinese Application Number 201811452816.2, filed Nov. 30, 2018, and Chinese Application Number 201811453568.3, filed Nov. 30, 2018.

TECHNICAL FIELD

The patent includes three kinds of moderate halophilic bacteria and a method for fermentation of fish paste by these three kinds of moderate halophilic bacteria. This patent belongs to the field of solid-state fermentation of aquatic products by microorganisms.

BACKGROUND

Chinese freshwater aquaculture is rapidly developing, but the development of freshwater fish processing industry is lagging behind. Therefore, the development of freshwater fish products suitable for the need of domestic consumer is very important to promote the healthy development of freshwater fish industry. The fermented aquatic products are popular in China and other countries in East Asia due to rich in amino acids, high nutrition. However, traditional fermented aquatic products have some problems such as long fermentation time, high salt content, and unstable product quality. Moderate halophile bacteria grow in NaCl concentration range from 0.5 mol/L to 2.5 mol/L. Compared with mild halophile bacteria, moderate halophile bacteria can grow in high-salt environment, reducing the contamination of spoilage bacteria during fermentation. Compared with the extreme halophilic bacteria, moderate halophilic bacteria have a more extensive halophilic range, wider distribution, more sources, and lower requirements for nutrients. Therefore, moderate halophilic bacteria are more adaptable to living environment and more accessible to be used in the fermentation of aquatic production. Furthermore, many moderate halophilic bacteria have strong ability to secrete extracellular protease. This patent provides a method to ferment fish paste in a short time by moderate halophilic bacteria. Moreover, the fermented fish paste is low salinity, intense flavor and high nutritional value. This patent provides a brand-new theoretical basis and a method for improving the fermentation quality of aquatic products.

SUMMARY

The patent utilizes the excellent characteristics of moderate halophilic bacteria and uses microbial fermentation method to produce a flavor fish paste. This method can effectively improve the flavor and nutrition of fish paste.

The moderate halophilic JD (*Bacillus aquimaris* JD) used in this patent is preserved in China General Microbiological Culture Collection Center (CGMCC) on Sep. 27, 2018. The collection number of the moderate halophilic JD is CGMCC NO. 16541, which is classified as *Bacillus aquimaris*.

A method for fermentation of fish paste by *Bacillus aquimaris* strain includes the following steps:
(1) Treatment of raw materials: fish meat is grounded by a chopper, and then sea salt 5~20% (w/w) is added, followed by a setting in 4° C. refrigerator for 5~24 h before fermentation.
(2) Preparation of moderate halophilic strains: *Bacillus aquimaris* CGMCC 16541, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris* CGMCC 16541 is mixed into the pre-treated raw fish paste. The final amount of bacteria is about $10^4$~$10^7$ CFU/g, which meets the requirement for the final number of bacteria.
(4) Fermentation of fish paste: the mixed material obtained in step (3) is fermented at 28~40° C. for 5~30 days, and then fermented fish paste is placed under −20° C. for next step.
(5) Stirring and ventilating during the fermentation of fish paste: The fermented fish paste is stirred clockwise for 1~5 min every 1~5 days under aseptic conditions during the 5~30 days of fermentation. After stirred, the fermented fish paste is set to breathe freely for 10~120 seconds.
(6) Cooking fish sauce: The fish paste obtained in step (4) is steamed in a steamer for 20~40 min until the fish paste is thoroughly cooked.
(7) Sterilization of fish paste: The cooked fish paste in step (6) is filled into cans, sealed, and sterilized at 120° C. for 15~20 min. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

The moderate halophilic JD (*Bacillus hwajinpoensis* JD) provided by the patent is preserved in China General Microbiological Culture Collection Center (CGMCC) on Sep. 27, 2018. The collection number of the moderate halophilic JD (*Bacillus hwajinpoensis* JD) is CGMCC NO. 16542, which is classified as *Bacillus hwajinpoensis*.

A method for fermentation of fish meat paste by *Bacillus hwajinpoensis* strains includes the following steps:
(1) Treatment of raw materials: fish meat is grounded by a chopper, and then sea salt 5~20% (w/w) is added, followed by a setting in 4° C. refrigerator for 5~24 h before fermentation.
(2) Preparation of moderate halophilic strains: *Bacillus hwajinpoensis* CGMCC 16542, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Bacillus hwajinpoensis* CGMCC 16542 is mixed into the pre-treated raw fish paste. The final amount of bacteria is about $10^4$~$10^7$ CFU/g, which meets the requirement for the final number of bacteria.

(4) Fermentation of fish paste: the mixed material obtained in step (3) is fermented at 28~40° C. for 5~30 days, and then fermented fish paste is placed under −20° C. for next step.

(5) Stirring and ventilating during the fermentation of fish paste: The fermented fish paste is stirred clockwise for 1~5 min every 1~5 days under aseptic conditions during the 5~30 days of fermentation. After stirred, the fermented fish paste is set to breathe freely for 10~120 seconds.

(6) Cooking fish sauce: The fish paste obtained in step (4) is steamed in a steamer for 20~40 min until the fish paste is thoroughly cooked.

(7) Sterilization of fish paste: The cooked fish paste in step (6) is filled into cans, sealed, and sterilized at 120° C. for 15~20 min. The fermented fish paste products are obtained.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

The moderately halophilic JD (*Halobacillus faecis* JD) provided by the patent is preserved in China General Microbiological Culture Collection Center (CGMCC) on Sep. 27, 2018. The collection number of the moderate halophilic JD (*Halobacillus faecis* JD) is CGMCC NO. 16543, which is classified as *Halobacillus faecis*.

A method for fermentation of fish meat paste by *Halobacillus faecis* strains includes the following steps:

(1) Treatment of raw materials: fish meat is grounded by a chopper, and then sea salt 5~20% (w/w) is added, followed by a setting in 4° C. refrigerator for 5~24 h before fermentation.

(2) Preparation of moderate halophilic strains: *Halobacillus faecis* CGMCC 16543, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Halobacillus faecis* CGMCC 16543 is mixed into the pre-treated raw fish paste. The final amount of bacteria is about $10^4$~$10^7$ CFU/g, which meets the requirement for the final number of bacteria.

(4) Fermentation of fish paste: the mixed material obtained in step (3) is fermented at 28~40° C. for 5~30 days, and then fermented fish paste is placed under −20° C. for next step.

(5) Stirring and ventilating during the fermentation of fish paste: The fermented fish paste is stirred clockwise for 1~5 min every 1~5 days under aseptic conditions during the 5~30 days of fermentation. After stirred, the fermented fish paste is set to breathe freely for 10~120 seconds.

(6) Cooking fish sauce: The fish paste obtained in step (4) is steamed in a steamer for 20~40 min until the fish paste is thoroughly cooked.

(7) Sterilization of fish paste: The cooked fish paste in step (6) is filled into cans, sealed, and sterilized at 120° C. for 15~20 min. The fermented fish paste products are obtained.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

The patent provides a method for fermenting fish paste by medium halophilic bacteria. The patent includes the processing of raw materials, preparation, and addition of mixed strains, fermentation of fish paste, determination of amino acid nitrogen, sensory evaluation, and other procedures. The specific production process is as follows:

The patent relates to a method of fermentation of fish paste by a mixed starter culture, characterized by the following steps:

(1) Treatment of raw materials: fish meat is grounded by a chopper, and then sea salt (5~20% (w/w) is added, followed by a setting in 4° C. refrigerator for 5~24 h before fermentation.

(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Bacillus aquimaris, Bacillus hwajinpoensis* and *Halobacillus faecis* are prepared into the mixed starter in proportion (1~3):(1~3):(1~3). The mixed starter culture is added to the pretreated raw fish paste in accordance with the bacteria addition amount ($10^4$~$10^7$ CFU/g), which meets the requirement for the final number of bacteria. Alternatively, the three strains are added to the raw fish, and the final bacterial count is in line with the addition ratio (1~3):(1~3):(1·3) and the final addition amount ($10^4$~$10^7$ CFU/g).

(4) Fermentation of fish paste: the mixed material obtained in step (3) is fermented at 28~40° C. for 5~30 days, and then fermented fish paste is placed under −20° C. for next step.

(5) Stirring and ventilating during the fermentation of fish paste: The fermented fish paste is stirred clockwise for 1~5 min every 1~5 days under aseptic conditions during the 5~30 days of fermentation. After stirred, the fermented fish paste is set to breathe freely for 10~120 seconds.

(6) Cooking fish sauce: The fish paste obtained in step (4) is steamed in a steamer for 20~40 min until the fish paste is thoroughly cooked.

(7) Sterilization of fish paste: The cooked fish paste in step (6) is filled into cans, sealed, and sterilized at 120° C. for 15~20 min. The fermented fish paste products are produced.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

The patent has the following advantages: (1) The fish paste fermented by moderate halophilic bacteria is low salinity, high content of amino acid nitrogen, delicious taste, and precious nutritional value. The total volatile basic nitrogen content of the fish paste is lower than the EU standard. Furthermore, the histamine content is far lower than Chinese national standard, so it is high quality and safety to ferment fish paste products. (2) The fermentation process of the above mixed fermentation starters in the fish paste fermentation, such as starter addition ratio, starter amount, fermentation time, fermentation temperature and salt addition amount, is optimized. The quality of the fish paste was comprehensively evaluated by the physical and chemical indicators and sensory indicators. The fish paste fermented by this method is low salinity, high content of amino acid nitrogen, delicious taste, and precious nutritional value. The total volatile basic nitrogen content of the fish paste is lower than the EU standard. Furthermore, the histamine content is far lower than Chinese national standard, so it is high quality and safety to ferment fish paste products.

DETAILED DESCRIPTION (一) *Bacillus Aquimaris*

1. Isolation and Screening of Bacterial Strains:

The salt-tolerant bacteria were isolated and screened from a traditional fermented fresh shrimp paste, which came from Heiyanzi town, Fengnan district, Tangshan, Hebei province, China. Isolation and purification of moderate halophilic bacteria using Gibbons medium with 1% skim milk powder. The shrimp paste diluted with sterile water is spread on the solid Gibbons medium and cultured at 30° C. for 48 h. The colonies with typical characteristics were selected, and further isolated and purified on the solid Gibbons medium with 1% skim milk powder for several times to obtain a single colony producing protease. The isolated and purified strains were inoculated on the Gibbons inclined plane, cultured at 30° C. for 48 h, and placed in a refrigerator at 4° C. for short-term storage.

Figure 1:
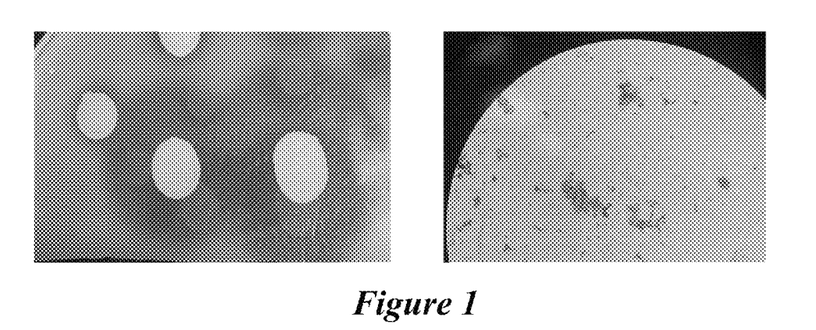
FIG. 1 shows the colony morphology of moderate halophilic *Bacillus aquimaris* JD.

2. Identification of Strains:

2.1. Morphological Characteristics of Strains (FIG. 1)

The colony is yellowish, smooth, neat, opaque and dense. The bacteria are rod-shaped. And gram staining is negative.

2.2. Physiological Characteristics of Strains

The strain can grow well in NaCl concentration range of 0~15%, at pH 7~9, and in the temperature range of 25° C.~43° C.

2.3. Molecular Biological Identification

Figure 2:
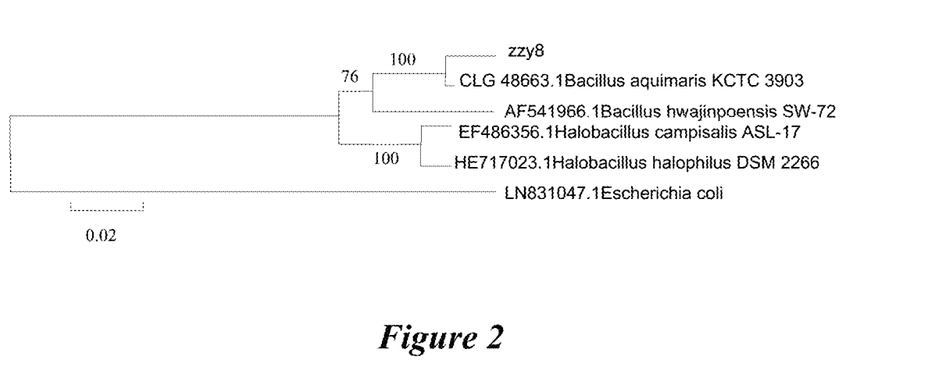
FIG. 2 shows phylogenetic tree constructed by 16S rRNA sequence of *Bacillus aquimaris* JD. Note: zzy8 is *Bacillus aquimaris* JD.

The isolated bacteria are sequenced with 16S rRNA. Tthe gene sequence obtained is retrieved in Ezbiocloud. Finally, the strain is identified as *Bacillus aquimaris*. The biological evolutionary relationship tree is constructed by the Mege5.1 program of DNAStar software. The result is shown in FIG. 2.

The moderately halophilic JD (*Bacillus aquimaris* JD) provided by the patent is preserved in China General Microbiological Culture Collection Center (CGMCC) on Sep. 27, 2018. The collection number of the moderate halophilic JD (*Bacillus aquimaris* JD) is CGMCC NO. 16541, which is classified as *Bacillus aquimaris*.

(二) *Bacillus Hwajinpoensis* 1. Isolation and Screening of Bacterial Strains

The salt-tolerant bacteria were isolated and screened from the traditional fermented fresh shrimp paste, which came from Heiyanzi town, Fengnan district, Tangshan, Hebei province, China. Isolation and purification of moderate halophilic bacteria using Gibbons medium with 1% skim milk powder. The shrimp paste diluted with sterile water is spread on the solid Gibbons medium and cultured at 30° C. for 48 h. The colonies with typical characteristics were selected, and further isolated and purified on the solid Gibbons medium with 1% skim milk powder for several times to obtain a single colony producing protease. The isolated and purified strains were inoculated on the Gibbons inclined plane, cultured at 30° C. for 48 h, and placed in a refrigerator at 4° C. for short-term storage.

Figure 3:
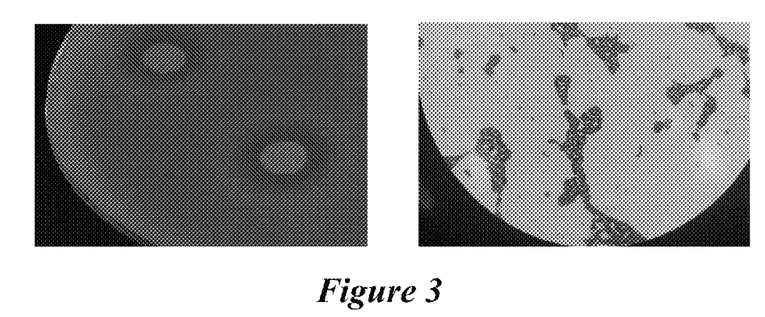
FIG. 3 shows the colony morphology of moderate halophilic *Bacillus hwajinpoensis* JD.

2. Identification of Strains:

2.1. Morphological Characteristics of Strains (FIG. 3)

The colony is yellowish, smooth, neat, opaque and dense. The bacteria are rod-shaped. And gram staining is negative.

2.2. Physiological Characteristics of Strains

The strain can grow well in NaCl concentration range of 0~15%, at pH 7~9, and in the temperature range of 25° C.~43° C.

2.3. Molecular Biological Identification

Figure 4:
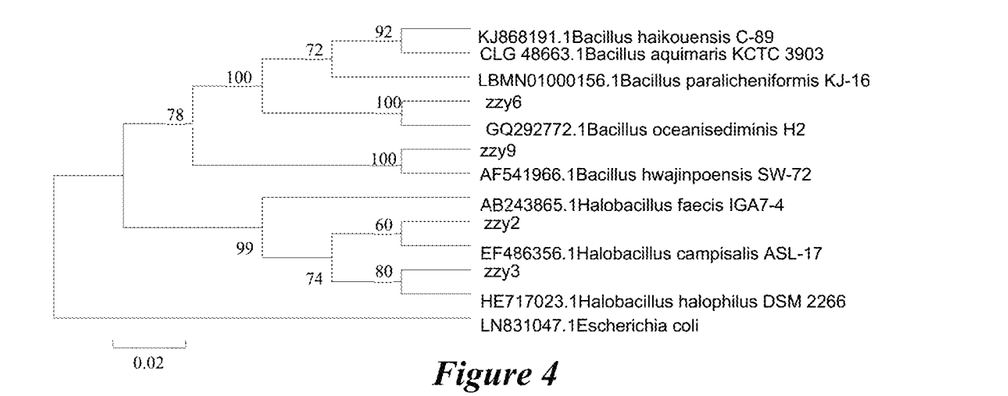
FIG. 4 shows phylogenetic tree constructed by 16S rRNA sequence of *Bacillus hwajinpoensis* JD. Note: zzy9 is *Bacillus hwajinpoensis* JD.

The isolated bacteria were sequenced with 16SrRNA, and the gene sequence obtained is processed and retrieved in Ezbiocloud. Finally, the strain is identified as *Bacillus*

*hwajinpoensis*. According to the homologous strains retrieved and using the Mege5.1 program of DNAStar software, the biological evolutionary relationship tree is constructed, as shown in FIG. 4.

The moderately halophilic JD (*Bacillus hwajinpoensis* JD) provided by the patent is preserved in China General Microbiological Culture Collection Center (CGMCC) on Sep. 27, 2018. The collection number of the moderate halophilic JD (*Bacillus hwajinpoensis* JD) is CGMCC NO. 16542, which is classified as *Bacillus hwajinpoensis*.

(三) *Halobacillus Faecis*

1. Isolation and Screening of Bacterial Strains

The salt-tolerant bacteria were isolated and screened from the traditional fermented fresh shrimp paste, which came from Heiyanzi town, Fengnan district, Tangshan, Hebei province, China. Isolation and purification of moderate halophilic bacteria using Gibbons medium with 1% skim milk powder. The shrimp paste diluted with sterile water is spread on the solid Gibbons medium and cultured at 30° C. for 48 h. The colonies with typical characteristics were selected, and further isolated and purified on the solid Gibbons medium with 1% skim milk powder for several times to obtain a single colony producing protease. The isolated and purified strains were inoculated on the Gibbons inclined plane, cultured at 30° C. for 48 h, and placed in a refrigerator at 4° C. for short-term storage.

Figure 5:
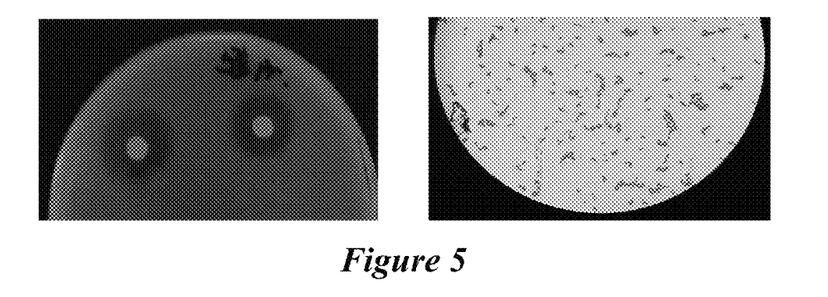
FIG. 5 shows the colony morphology of moderate halophilic *Halobacillus faecis* JD.

2. Identification of Strains:

2.1. Morphological Characteristics of Strains (FIG. 5)

The colony is yellowish, smooth, neat, opaque and dense. The bacteria are rod-shaped. And gram staining is negative.

2.2. Physiological Characteristics of Strains

The strain can grow well in NaCl concentration range of 0~15%, at pH 7~9, and in the temperature range of 25° C.~43° C.

2.3. Molecular Biological Identification

Figure 6:
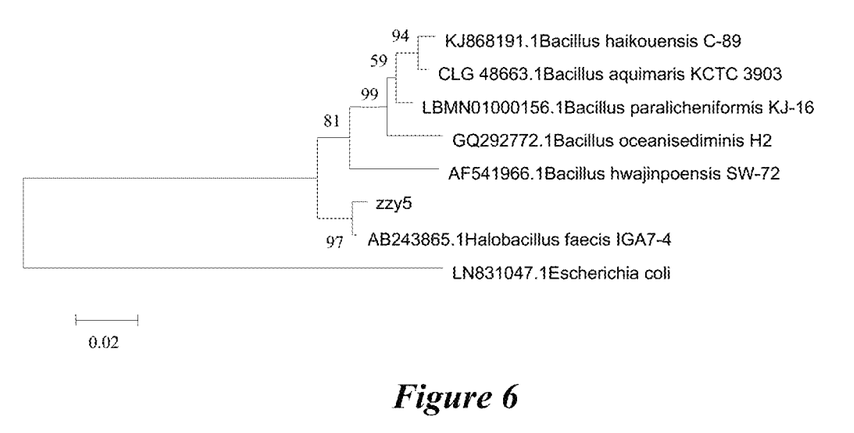
FIG. 6 shows phylogenetic tree constructed by 16S rRNA sequence of *Halobacillus faecis* JD. Note: zzy5 is *Halobacillus faecis* JD.

The isolated bacteria were sequenced with 16SrRNA, and the gene sequence obtained is processed and retrieved in Ezbiocloud. Finally, the strain is identified as *Bacillus hwajinpoensis*. According to the homologous strains retrieved and using the Mege5.1 program of DNAStar software, the biological evolutionary relationship tree is constructed, as shown in FIG. 6.

The moderately halophilic JD (*Halobacillus faecis* JD) provided by the patent is preserved in China General Microbiological Culture Collection Center (CGMCC) on Sep. 27, 2018. The collection number of the moderate halophilic JD (*Halobacillus faecis* JD) is CGMCC NO. 16543, which is classified as *Halobacillus faecis*.

Embodiment 1

A method for fermentation of fish meat paste by *Bacillus aquimaris* strains follows the following steps:
(1) Treatment of raw materials: fish meat is grounded by a chopper, and then sea salt 5% (w/w) is added, followed by a setting in 4° C. refrigerator for 5~24 h before fermentation.
(2) Preparation of moderate halophilic strains: *Bacillus aquimaris* CGMCC 16541, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris* CGMCC 16541 is mixed into the pre-treated raw fish paste. The final amount of bacteria is about $10^4$ CFU/g, which meets the requirement for the final number of bacteria.
(4) Fermentation of fish paste: the mixed material obtained in step (3) is fermented at 28° C. for 30 days, and then fermented fish paste is placed under −20° C. for next step.
(5) Stirring and ventilating during the fermentation of fish paste: The fermented fish paste is stirred clockwise for 1 min every 5 days under aseptic conditions during the 30 days of fermentation. After stirred, the fermented fish paste is set to breathe freely for 10 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.643 g/100 g. The content of volatile base nitrogen is 25.32 mg/100 g, which is lower than the EU standard (35 mg/100 g). The histamine content is 3.77 mg/100 g, much lower than Chinese national standard (20 mg/100 g). The sensory evaluation score of fish sauce with this strain is 6.27, while that of fish sauce without this strain is 5.69. Compared with the fish paste without added strain, the flavor of the fish paste is significantly improved.

Embodiment 2

A method for fermentation of fish meat paste by *Bacillus aquimaris* strains follows the following steps:
(1) Treatment of raw materials: fish meat is grounded by a chopper, and then sea salt 20% (w/w) is added, followed by a setting in 4° C. refrigerator for 5~24 h before fermentation.
(2) Preparation of moderate halophilic strains: *Bacillus aquimaris* CGMCC 16541, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris* CGMCC 16541 is mixed into the pre-treated raw fish paste. The final amount of bacteria is about $10^7$ CFU/g, which meets the requirement for the final number of bacteria.
(4) Fermentation of fish paste: the mixed material obtained in step (3) is fermented at 40° C. for 5 days, and then fermented fish paste is placed under −20° C. for next step.
(5) Stirring and ventilating during the fermentation of fish paste: The fermented fish paste is stirred clockwise for 5 min every 1 day under aseptic conditions during the 5 days of fermentation. After stirred, the fermented fish paste is set to breathe freely for 120 seconds.
(6) Cooking fish sauce: The fish paste obtained in step (4) is steamed in a steamer for 40 min until the fish paste is thoroughly cooked.
(7) Sterilization of fish paste: The cooked fish paste in step (6) is filled into cans, sealed, and sterilized for 20 min at 120° C. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.307 g/100 g. The content of volatile base nitrogen is 7.57 mg/100 g, which is lower than the EU standard (35 mg/100 g). The histamine content is 2.01 mg/100 g, much lower than Chinese national standard (20 mg/100 g). The sensory evaluation score of fish sauce with this strain is 5.88, while that of fish sauce without this strain is 5.49. Compared with the fish paste without added strain, the flavor of the fish paste is significantly improved.

Embodiment 3

A method for fermentation of fish meat paste by *Bacillus hwajinpoensis* strains follows the following steps:
(1) Treatment of raw materials: fish meat is grounded by a chopper, and then sea salt 5% (w/w) is added, followed by a setting in 4° C. refrigerator for 5~24 h before fermentation.
(2) Preparation of moderate halophilic strains: *Bacillus hwajinpoensis* CGMCC 16542, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus hwajinpoensis* CGMCC 16542 is mixed into the pre-treated raw fish paste. The final amount of bacteria is about $10^4$ CFU/g, which meets the requirement for the final number of bacteria.

(4) Fermentation of fish paste: the mixed material obtained in step (3) is fermented at 28° C. for 30 days, and then fermented fish paste is placed under −20° C. for next step.
(5) Stirring and ventilating during the fermentation of fish paste: The fermented fish paste is stirred clockwise for 1 min every 5 days under aseptic conditions during the 30 days of fermentation. After stirred, the fermented fish paste is set to breathe freely for 10 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.639 g/100 g. The content of volatile base nitrogen is 24.87 mg/100 g, which is lower than the EU standard (35 mg/100 g). The histamine content is 3.82 mg/100 g, much lower than Chinese national standard (20 mg/100 g). The sensory evaluation score of fish sauce with this strain is 6.33, while that of fish sauce without this strain is 5.67. Compared with the fish paste without added strain, the flavor of the fish paste is significantly improved.

Embodiment 4

A method for fermentation of fish meat paste by *Bacillus hwajinpoensis* strains follows the following steps:
(1) Treatment of raw materials: fish meat is grounded by a chopper, and then sea salt 20% (w/w) is added, followed by a setting in 4° C. refrigerator for 5~24 h before fermentation.
(2) Preparation of moderate halophilic strains: *Bacillus hwajinpoensis* CGMCC 16542, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus hwajinpoensis* CGMCC 16542 is mixed into the pre-treated raw fish paste. The final amount of bacteria is about $10^7$ CFU/g, which meets the requirement for the final number of bacteria.
(4) Fermentation of fish paste: the mixed material obtained in step (3) is fermented at 40° C. for 5 days, and then fermented fish paste is placed under −20° C. for next step.

(5) Stirring and ventilating during the fermentation of fish paste: The fermented fish paste is stirred clockwise for 5 min every 1 day under aseptic conditions during the 5 days of fermentation. After stirred, the fermented fish paste is set to breathe freely for 120 seconds.
(6) Cooking fish sauce: The fish paste obtained in step (4) is steamed in a steamer for 40 min until the fish paste is thoroughly cooked.
(7) Sterilization of fish paste: The cooked fish paste in step (6) is filled into cans, sealed, and sterilized at 120° C. for 20 min. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.312 g/100 g. The content of volatile base nitrogen is 7.80 mg/100 g, which is lower than the EU standard (35 mg/100 g). The histamine content is 1.98 mg/100 g, much lower than Chinese national standard (20 mg/100 g). The sensory evaluation score of fish sauce with this strain is 5.93, while that of fish sauce without this strain is 5.48. Compared with the fish paste without added strain, the flavor of the fish paste is significantly improved.

Embodiment 5

A method for fermentation of fish meat paste by *Halobacillus faecis* strains follows the following steps:
(1) Treatment of raw materials: fish meat is grounded by a chopper, and then sea salt 5 (w/w) is added, followed by a setting in 4° C. refrigerator for 5~24 h before fermentation.
(2) Preparation of moderate halophilic strains: *Halobacillus faecis* CGMCC 16543, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Halobacillus faecis* CGMCC 16543 is mixed into the pre-treated raw fish paste. The final amount of bacteria is about $10^4$ CFU/g, which meets the requirement for the final number of bacteria.
(4) Fermentation of fish paste: the mixed material obtained in step (3) is fermented at 28° C. for 30 days, and then fermented fish paste is placed under −20° C. for next step.
(5) Stirring and ventilating during the fermentation of fish paste: The fermented fish paste is stirred clockwise for 1 min every 5 days under aseptic conditions during the 30 days of fermentation. After stirred, the fermented fish paste is set to breathe freely for 10~120 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are obtained.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.647 g/100 g. The content of volatile base nitrogen is 24.82 mg/100 g, which is lower than the EU standard (35 mg/100 g). The histamine content is 3.81 mg/100 g, much lower than Chinese national standard (20 mg/100 g). The sensory evaluation score of fish sauce with this strain is 6.32, while that of fish sauce without this strain is 5.66. Compared with the fish paste without added strain, the flavor of the fish paste is significantly improved.

Embodiment 6

A method for fermentation of fish meat paste by *Halobacillus faecis* strains follows the following steps:
(1) Treatment of raw materials: fish meat is grounded by a chopper, and then sea salt 20% (w/w) is added, followed by a setting in 4° C. refrigerator for 5~24 h before fermentation.
(2) Preparation of moderate halophilic strains: *Halobacillus faecis* CGMCC 16543, a moderate halophilic strain, is inoculated and activated in the culture medium, and the operation is repeated for three times. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Halobacillus faecis* CGMCC 16543 is mixed into the pre-treated raw fish paste. The final amount of bacteria is about $10^7$ CFU/g, which meets the requirement for the final number of bacteria.
(4) Fermentation of fish paste: the mixed material obtained in step (3) is fermented at 40° C. for 5 days, and then fermented fish paste is placed under −20° C. for next step.
(5) Stirring and ventilating during the fermentation of fish paste: The fermented fish paste is stirred clockwise for 5 min every 1 day under aseptic conditions during the 5 days of fermentation. After stirred, the fermented fish paste is set to breathe freely for 120 seconds.
(6) Cooking fish sauce: The fish paste obtained in step (4) is steamed in a steamer for 40 min until the fish paste is thoroughly cooked.

(7) Sterilization of fish paste: The cooked fish paste in step (6) is filled into cans, sealed, and sterilized at 120° C. for 20 min. The fermented fish paste products are obtained.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

(10) Physicochemical indexes and sensory evaluation of fish paste: The content of amino acid nitrogen in fish sauce fermented by this strain is 0.314 g/100 g. The content of volatile base nitrogen is 7.63 mg/100 g, which is lower than the EU standard (35 mg/100 g). The histamine content is 2.11 mg/100 g, much lower than Chinese national standard (20 mg/100 g). The sensory evaluation score of fish sauce with this strain is 5.94, while that of fish sauce without this strain is 5.53. Compared with the fish paste without added strain, the flavor of the fish paste is significantly improved.

Embodiment 7

The patent relates to a method of fermentation of fish paste by a mixed starter culture, characterized by the following steps:

(1) Treatment of raw materials: fish meat is grounded by a chopper, and then sea salt 12% (w/w) is added, followed by a setting in 4° C. refrigerator for 5~24 h before fermentation.

(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Bacillus aquimaris, Bacillus hwajinpoensis* and *Halobacillus faecis* are prepared into the mixed starter in proportion 2:1:1. The mixed starter culture is added to the pretreated raw fish paste in accordance with the bacteria addition amount $10^4$ CFU/g, which meets the requirement for the final number of bacteria. Alternatively, the three strains are added to the raw fish, and the final bacterial count is in line with the addition ratio 2:1:1 and the final addition amount $10^4$ CFU/g.

(4) Fermentation of fish paste: the mixed material obtained in step (3) is fermented at 40° C. for 5 days, and then fermented fish paste is placed under −20° C. for next step.

(5) Stirring and ventilating during the fermentation of fish paste: The fermented fish paste is stirred clockwise for 2 min every 1 day under aseptic conditions during the 5 days of fermentation. After stirred, the fermented fish paste is set to breathe freely for 30 seconds.

(6) Cooking fish sauce: The fish paste obtained in step (4) is steamed in a steamer for 20 min until the fish paste is thoroughly cooked.

(7) Sterilization of fish paste: The cooked fish paste in step (6) is filled into cans, sealed, and sterilized at 120° C. for 15 min. The fermented fish paste products are produced.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

(10) Physicochemical indexes and sensory evaluation of fish paste: The content of amino acid nitrogen in fish sauce fermented by this strain is 0.311 g/100 g. The content of volatile base nitrogen is 7.54 mg/100 g, which is lower than the EU standard (35 mg/100 g). The histamine content is 1.69 mg/100 g, much lower than Chinese national standard (20 mg/100 g). The sensory evaluation score of fish sauce with this strain is 5.79. Compared with the fish paste without added strain, the flavor of the fish paste is significantly improved.

Embodiment 8

The patent relates to a method of fermentation of fish paste by a mixed starter culture, characterized by the following steps:

(1) Treatment of raw materials: fish meat is grounded by a chopper, and then sea salt 12% (w/w) is added, followed by a setting in 4° C. refrigerator for 5~24 h before fermentation.

(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Bacillus aquimaris, Bacillus hwajinpoensis* and *Halobacillus faecis* are prepared into the mixed starter in proportion 1:1:1. The mixed starter culture is added to the pretreated raw fish paste in accordance with the bacteria addition amount $10^6$ CFU/g, which meets the requirement for the final number of bacteria. Alternatively, the three strains are added to the raw fish, and the final bacterial count is in line with the addition ratio 1:1:1 and the final addition amount $10^6$ CFU/g.

(4) Fermentation of fish paste: the mixed material obtained in step (3) is fermented at 37° C. for 15 days, and then fermented fish paste is placed under −20° C. for next step.

(5) Stirring and ventilating during the fermentation of fish paste: The fermented fish paste is stirred clockwise for 2 min every 5 days under aseptic conditions during the 15 days of fermentation. After stirred, the fermented fish paste is set to breathe freely for 30 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are produced.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.519 g/100 g. The content of volatile base nitrogen is 23.86 mg/100 g, which is lower than the EU standard (35 mg/100 g). The histamine content is 2.17 mg/100 g, much lower than Chinese national standard (20 mg/100 g). The sensory evaluation score of fish sauce with this strain is 7.20. Compared with the fish paste without added strain, the flavor of the fish paste is significantly improved.

Embodiment 9

The patent relates to a method of fermentation of fish paste by a mixed starter culture, characterized by the following steps:
(1) Treatment of raw materials: fish meat is grounded by a chopper, and then sea salt 14% (w/w) is added, followed by a setting in 4° C. refrigerator for 5~24 h before fermentation.
(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris, Bacillus hwajinpoensis* and *Halobacillus faecis* are prepared into the mixed starter in proportion 1:1:1. The mixed starter culture is added to the pretreated raw fish paste in accordance with the bacteria addition amount $10^5$ CFU/g, which meets the requirement for the final number of bacteria. Alternatively, the three strains are added to the raw fish, and the final bacterial count is in line with the addition ratio 1:1:1 and the final addition amount $10^5$ CFU/g.
(4) Fermentation of fish paste: the mixed material obtained in step (3) is fermented at 31° C. for 15 days, and then fermented fish paste is placed under −20° C. for next step.
(5) Stirring and ventilating during the fermentation of fish paste: The fermented fish paste is stirred clockwise for 2 min every 5 days under aseptic conditions during the 15 days of fermentation. After stirred, the fermented fish paste is set to breathe freely for 30 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are produced.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.476 g/100 g. The content of volatile base nitrogen is 20.11 mg/100 g, which is lower than the EU standard (35 mg/100 g). The histamine content is 1.92 mg/100 g, much lower than Chinese national standard (20 mg/100 g). The sensory evaluation score of fish sauce with this strain is 6.62. Compared with the fish paste without added strain, the flavor of the fish paste is significantly improved.

Embodiment 10

The patent relates to a method of fermentation of fish paste by a mixed starter culture, characterized by the following steps:
(1) Treatment of raw materials: fish meat is grounded by a chopper, and then sea salt 20% (w/w) is added, followed by a setting in 4° C. refrigerator for 5-24 h before fermentation.
(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris, Bacillus hwajinpoensis* and *Halobacillus faecis* are prepared into the mixed starter in proportion 3:1:1. The mixed starter culture is added to the pretreated raw fish paste in accordance with the bacteria addition amount $10^7$ CFU/g, which meets the requirement for the final number of bacteria. Alternatively, the three strains are added to the raw fish, and the final bacterial count is in line with the addition ratio 3:1:1 and the final addition amount $10^7$ CFU/g.

(4) Fermentation of fish paste: the mixed material obtained in step (3) is fermented at 40° C. for 30 days, and then fermented fish paste is placed under −20° C. for next step.

(5) Stirring and ventilating during the fermentation of fish paste: The fermented fish paste is stirred clockwise for 2 min every 5 days under aseptic conditions during the 30 days of fermentation. After stirred, the fermented fish paste is set to breathe freely for 30 seconds.

(6) Cooking fish sauce: The fish paste obtained in step (4) is steamed in a steamer for 20 min until the fish paste is thoroughly cooked.

(7) Sterilization of fish paste: The cooked fish paste in step (6) is filled into cans, sealed, and sterilized at 120° C. for 15 min. The fermented fish paste products are produced.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

(10) Physicochemical indexes and sensory evaluation of fish paste: The content of amino acid nitrogen in fish sauce fermented by this strain is 0.621 g/100 g. The content of volatile base nitrogen is 39.81 mg/100 g, which is lower than the EU standard (35 mg/100 g). The histamine content is 6.98 mg/100 g, much lower than Chinese national standard (20 mg/100 g). The sensory evaluation score of fish sauce with this strain is 5.87. Compared with the fish paste without added strain, the flavor of the fish paste is significantly improved.

Embodiment 11

The patent relates to a method of fermentation of fish paste by a mixed starter culture, characterized by the following steps:

(1) Treatment of raw materials: fish meat is grounded by a chopper, and then sea salt 5% (w/w) is added, followed by a setting in 4° C. refrigerator for 5-24 h before fermentation.

(2) Preparation of mixed starter culture: *Bacillus aquimaris*, *Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5 \sim 10^6$ CFU/mL, and the bacterial liquid is stored at 4° C., and used within 24 h.

(3) Adding of starter culture: *Bacillus aquimaris*, *Bacillus hwajinpoensis* and *Halobacillus faecis* are prepared into the mixed starter in proportion 2:2:1. The mixed starter culture is added to the pretreated raw fish paste in accordance with the bacteria addition amount $10^6$ CFU/g, which meets the requirement for the final number of bacteria. Alternatively, the three strains are added to the raw fish, and the final bacterial count is in line with the addition ratio 2:2:1 and the final addition amount $10^6$ CFU/g.

(4) Fermentation of fish paste: the mixed material obtained in step (3) is fermented at 28° C. for 5 days, and then fermented fish paste is placed under −20° C. for next step.

(5) Stirring and ventilating during the fermentation of fish paste: The fermented fish paste is stirred clockwise for 2 min every 1 day under aseptic conditions during the 5 days of fermentation. After stirred, the fermented fish paste is set to breathe freely for 30 seconds.

(6) Cooking fish sauce: The fish paste obtained in step (4) is steamed in a steamer for 20 min until the fish paste is thoroughly cooked.

(7) Sterilization of fish paste: The cooked fish paste in step (6) is filled into cans, sealed, and sterilized at 120° C. for 15 min. The fermented fish paste products are produced.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

(10) Physicochemical indexes and sensory evaluation of fish paste: The content of amino acid nitrogen in fish sauce fermented by this strain is 0.362 g/100 g. The content of volatile base nitrogen is 6.49 mg/100 g, which is lower than the EU standard (35 mg/100 g). The histamine content is 1.13 mg/100 g, much lower than Chinese national standard (20 mg/100 g). The sensory evaluation score of fish sauce with this strain is 6.11. Compared with the fish paste without added strain, the flavor of the fish paste is significantly improved.

Embodiment 12

The patent relates to a method of fermentation of fish paste by a mixed starter culture, characterized by the following steps:

(1) Treatment of raw materials: fish meat is grounded by a chopper, and then sea salt 16% (w/w) is added, followed by a setting in 4° C. refrigerator for 5-24 h before fermentation.

(2) Preparation of mixed starter culture: *Bacillus aquimaris*, *Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5 \sim 10^6$ CFU/mL, and the bacterial liquid is stored at 4° C., and used within 24 h.

(3) Adding of starter culture: *Bacillus aquimaris*, *Bacillus hwajinpoensis* and *Halobacillus faecis* are prepared into the mixed starter in proportion 2:1:1. The mixed starter culture is added to the pretreated raw fish paste in accordance with the bacteria addition amount $10^6$ CFU/g, which meets the requirement for the final number of bacteria. Alternatively, the three strains are added to the raw fish paste respectively, and the final bacterial count is in line with the addition ratio 2:1:1 and the final addition amount $10^6$ CFU/g.
(4) Fermentation of fish paste: the mixed material obtained in step (3) is fermented at 31° C. for 20 days, and then fermented fish paste is placed under −20° C. for next step.
(5) Stirring and ventilating during the fermentation of fish paste: The fermented fish paste is stirred clockwise for 2 min every 5 days under aseptic conditions during the 20 days of fermentation. After stirred, the fermented fish paste is set to breathe freely for 30 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are produced.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.501 g/100 g. The content of volatile base nitrogen is 23.17 mg/100 g, which is lower than the EU standard (35 mg/100 g). The histamine content is 2.48 mg/100 g, much lower than Chinese national standard (20 mg/100 g). The sensory evaluation score of fish sauce with this strain is 6.94. Compared with the fish paste without added strain, the flavor of the fish paste is significantly improved.

Embodiment 13

The patent relates to a method of fermentation of fish paste by a mixed starter culture, characterized by the following steps:
(1) Treatment of raw materials: fish meat is grounded by a chopper, and then sea salt 20% (w/w) is added, followed by a setting in 4° C. refrigerator for 5-24 h before fermentation.
(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.
(3) Adding of starter culture: *Bacillus aquimaris, Bacillus hwajinpoensis* and *Halobacillus faecis* are prepared into the mixed starter in proportion 2:2:1. The mixed starter culture is added to the pretreated raw fish paste in accordance with the bacteria addition amount $10^5$ CFU/g, which meets the requirement for the final number of bacteria. Alternatively, the three strains are added to the raw fish paste respectively, and the final bacterial count is in line with the addition ratio 2:2:1 and the final addition amount $10^5$ CFU/g.
(4) Fermentation of fish paste: the mixed material obtained in step (3) is fermented at 34° C. for 10 days, and then fermented fish paste is placed under −20° C. for next step.
(5) Stirring and ventilating during the fermentation of fish paste: The fermented fish paste is stirred clockwise for 2 min every 5 days under aseptic conditions during the 10 days of fermentation. After stirred, the fermented fish paste is set to breathe freely for 30 seconds.
(6) Cooking fish sauce: The fish paste obtained in step (4) is steamed in a steamer for 20 min until the fish paste is thoroughly cooked.
(7) Sterilization of fish paste: The cooked fish paste in step (6) is filled into cans, sealed, and sterilized at 120° C. for 15 min. The fermented fish paste products are produced.
(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;
(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.
(10) Physicochemical indexes and sensory evaluation of fish paste: The content of amino acid nitrogen in fish sauce fermented by this strain is 0.287 g/100 g. The content of volatile base nitrogen is 16.23 mg/100 g, which is lower than the EU standard (35 mg/100 g). The histamine content is 1.88 mg/100 g, much lower than Chinese national standard (20 mg/100 g). The sensory evaluation score of fish sauce with this strain is 5.97. Compared with the fish paste without added strain, the flavor of the fish paste is significantly improved.

Embodiment 14

The patent relates to a method of fermentation of fish paste by a mixed starter culture, characterized by the following steps:
(1) Treatment of raw materials: fish meat is grounded by a chopper, and then sea salt 10% (w/w) is added, followed by a setting in 4° C. refrigerator for 5-24 h before fermentation.
(2) Preparation of mixed starter culture: *Bacillus aquimaris, Bacillus hwajinpoensis* and *Halobacillus faecis* are inoculated in different culture media for three times, respectively. The cultured bacterial liquid is centrifuged at 10000 r/min for 10 min at 4° C. The precipitation is washed twice with sterile normal saline, and then suspended in sterile normal saline again. Finally, the concentration of bacterial liquid is adjusted to $10^5$~$10^6$ CFU/mL, and the bacterial liquid is stored at 4° C., and used within 24 h.

(3) Adding of starter culture: *Bacillus aquimaris*, *Bacillus hwajinpoensis* and *Halobacillus faecis* are prepared into the mixed starter in proportion 1:1:3. The mixed starter culture is added to the pretreated raw fish paste in accordance with the bacteria addition amount $10^4$ CFU/g, which meets the requirement for the final number of bacteria. Alternatively, the three strains are added to the raw fish, and the final bacterial count is in line with the addition ratio 1:1:3 and the final addition amount $10^4$ CFU/g.

(4) Fermentation of fish paste: the mixed material obtained in step (3) is fermented at 34° C. for 15 days, and then fermented fish paste is placed under −20° C. for next step.

(5) Stirring and ventilating during the fermentation of fish paste: The fermented fish paste is stirred clockwise for 2 min every 5 days under aseptic conditions during the 15 days of fermentation. After stirred, the fermented fish paste is set to breathe freely for 30 seconds.

(6) Cooking fish sauce: The fish paste obtained in step (4) is steamed in a steamer for 20 min until the fish paste is thoroughly cooked.

(7) Sterilization of fish paste: The cooked fish paste in step (6) is filled into cans, sealed, and sterilized at 120° C. for 15 min. The fermented fish paste products are produced.

(8) Evaluation of physical and chemical indices: The method for evaluating the amino acid nitrogen content is referred to GB5009.235-2016. The method for evaluating volatile base nitrogen content is referred to GB5009.228-2016. The method for evaluating histamine content is referred to GB5009.208-2016;

(9) Sensory evaluation: The sensory evaluation team is made up of 10 people, and the members of the team are required to conduct flavor training before the evaluation. The scores ranged from 0 to 9, with an overall rating for fishy, fermented, ammonia, umami, salty, sweet and bitter flavors.

(10) Physicochemical indexes and sensory evaluation of fish paste: The content of amino acid nitrogen in fish sauce fermented by this strain is 0.549 g/100 g. The content of volatile base nitrogen is 21.90 mg/100 g, which is lower than the EU standard (35 mg/100 g). The histamine content is 1.97 mg/100 g, much lower than Chinese national standard (20 mg/100 g). The sensory evaluation score of fish sauce with this strain is 6.34. Compared with the fish paste without added strain, the flavor of the fish paste is significantly improved.

The invention claimed is:

1. A method of fermentation of fish paste by *Bacillus aquimaris* moderate halophilic strain, whose preservation number is CGMCC NO. 16541, and whose proposed classification is *Bacillus aquimaris*, wherein the method is performed according to the following steps: the steps of:
   (1) treatment of raw materials: fish meat is grounded by a chopper, and then sea salt (5-20% (w/w)) is added, followed by a setting in 4° C. refrigerator for 5~24 h before fermentation;
   (2) preparation of moderate halophilic strains: *Bacillus aquimaris* CGMCC 16541, a moderate halophilic strain, is inoculated and activated in the culture medium, and the operation is repeated for three times; the cultured bacterial liquid is centrifuged at 10000 r/min for 10 min at 4° C.; the precipitation is washed twice with sterile normal saline, and then suspended in sterile normal saline again; finally, the concentration of bacterial liquid is adjusted to $10^5$~$10^6$ CFU/mL, and the bacterial liquid is stored at 4° C., and used within 24 h;
   (3) adding of starter culture: *Bacillus aquimaris* CGMCC 16541 is mixed into the pre-treated raw fish paste; the final amount of bacteria is about $10^4$~$10^7$ CFU/g,
   (4) Fermentation of fish paste: the mixed material obtained in step (3) is fermented at 28~40° C. for 5~30 days, and then fermented fish paste is placed under −20° C. for next step;
   (5) stirring and ventilating during the fermentation of fish paste: the fermented fish paste is stirred clockwise for 1~5 minutes at intervals of 1~5 days under aseptic conditions during the 5~30 days of fermentation; after stirred, the fermented fish paste is set to breathe freely for 10~120 seconds;
   (6) cooking fish sauce: the fish paste obtained in step (4) is steamed in a steamer for 20~40 minutes until the fish paste is thoroughly cooked;
   (7) sterilization of fish paste: the cooked fish paste in step (6) is filled into cans, sealed, and sterilized for 15~20 min at 120° C.; the fermented fish paste products are obtained.

2. A method of fermentation of fish paste by *Bacillus hwajinpoensis* moderate halophilic strain, whose preservation number is CGMCC NO. 16542, and whose proposed classification is *Bacillus hwajinpoensis*, wherein the method is performed according to the following steps:
   (1) treatment of raw materials: fish meat is grounded by a chopper, and then sea salt (5~20% (w/w)) is added, followed by a setting in 4° C. refrigerator for 5~24 h before fermentation;
   (2) preparation of moderate halophilic strains: *Bacillus hwajinpoensis* CGMCC 16542, a moderate halophilic strain, is inoculated and activated in the culture medium, and the operation is repeated for three times; the cultured bacterial liquid is centrifuged at 10000 r/min for 10 min at 4° C.; the precipitation is washed twice with sterile normal saline, and then suspended in sterile normal saline again; finally, the concentration of bacterial liquid is adjusted to $10^5$~$10^6$ CFU/mL, and the bacterial liquid is stored at 4° C., and used within 24 h;
   (3) adding of starter culture: *Bacillus hwajinpoensis* CGMCC 16542 is mixed into the pre-treated raw fish paste; the final amount of bacteria is about $10^4$~$10^7$ CFU/g, which meets the requirement for the final number of bacteria;
   (4) fermentation of fish paste: the mixed material obtained in step (3) is fermented at 28~40° C. for 5~30 days, and then fermented fish paste is placed under −20° C. for next step;
   (5) stirring and ventilating during the fermentation of fish paste: the fermented fish paste is stirred clockwise for 1~5 minutes at intervals of 1~5 days under aseptic conditions during the 5~30 days of fermentation; after stirred, the fermented fish paste is set to breathe freely for 10~120 seconds;
   (6) cooking fish sauce: the fish paste obtained in step (4) is steamed in a steamer for 20~40 minutes until the fish paste is thoroughly cooked;
   (7) sterilization of fish paste: the cooked fish paste in step (6) is filled into cans, sealed, and sterilized for 15~20 min at 120° C.; the fermented fish paste products are obtained.

3. A method of fermentation of fish paste by *Halobacillus faecis* moderate halophilic strain, whose preservation number is CGMCC NO. 16543, and whose proposed classification is *Halobacillus faecis*, wherein the method is performed according to the following steps:
   (1) treatment of raw materials: fish meat is grounded by a chopper, and then sea salt (5~20% (w/w)) is added, followed by a setting in 4° C. refrigerator for 5~24 h before fermentation;
   (2) preparation of moderate halophilic strains: *Halobacillus faecis* CGMCC 16543, a moderate halophilic strain, is inoculated and activated in the culture medium, and the operation is repeated for three times; the cultured bacterial liquid is centrifuged at 10000 r/min for 10 min at 4° C.; the precipitation is washed twice with sterile normal saline, and then suspended in sterile normal saline again; finally, the concentration of bacterial liquid is adjusted to $10^5$~$10^6$ CFU/mL, and the bacterial liquid is stored at 4° C., and used within 24 h;
   (3) adding of starter culture: *Halobacillus faecis* CGMCC 16543 is mixed into the pre-treated raw fish paste; the final amount of bacteria is about $10^4$~$10^7$ CFU/g, which meets the requirement for the final number of bacteria;
   (4) fermentation of fish paste: the mixed material obtained in step (3) is fermented at 28~40° C. for 5~30 days, and then fermented fish paste is placed under −20° C. for next step;
   (5) stirring and ventilating during the fermentation of fish paste: the fermented fish paste is stirred clockwise for 1~5 minutes at intervals of 1~5 days under aseptic conditions during the 5~30 days of fermentation; after stirred, the fermented fish paste is set to breathe freely for 10~120 seconds;
   (6) cooking fish sauce: the fish paste obtained in step (4) is steamed in a steamer for 20~40 minutes until the fish paste is thoroughly cooked;
   (7) sterilization of fish paste: the cooked fish paste in step (6) is filled into cans, sealed, and sterilized for 15~20 min at 120° C.; the fermented fish paste products are obtained.

4. A method of fermentation of fish paste by a mixed starter culture comprising the steps of:
   (1) treatment of raw materials: fish meat is grounded by a chopper, and then sea salt (5~20% (w/w)) is added, followed by a setting in 4° C. refrigerator for 5~24 h before fermentation;
   (2) preparation of mixed starter culture: *Bacillus aquimaris*, *Bacillus hwajinpoensis* and *Halobacillus faecis* are inoculated in different culture media for three times, respectively; the cultured bacterial liquid is centrifuged at 10000 r/min for 10 min at 4° C.; the precipitation is washed twice with sterile normal saline, and then suspended in sterile normal saline again; finally, the concentration of bacterial liquid is adjusted to $10^5$~$10^6$ CFU/mL, and the bacterial liquid is stored at 4° C., and used within 24 h;
   (3) adding of starter culture: *Bacillus aquimaris*, *Bacillus hwajinpoensis* and *Halobacillus faecis* are prepared into the mixed starter in proportion (1~3):(1~3):(1~3); the mixed starter culture is added to the pretreated raw fish paste in accordance with the bacteria addition amount ($10^4$~$10^7$ CFU/g), which meets the requirement for the final number of bacteria; alternatively, the three strains were added to the raw fish, and the final bacterial count was in line with the addition ratio (1~3):(1~3):(1~3) and the final addition amount ($10^4$~$10^7$ CFU/g);
   (4) fermentation of fish paste: the mixed material obtained in step (3) is fermented at 28~40° C. for 5~30 days, and then fermented fish paste is placed under −20° C. for next step;
   (5) stirring and ventilating during the fermentation of fish paste: the fermented fish paste is stirred clockwise for 1~5 minutes at intervals of 1~5 days under aseptic conditions during the 5~30 days of fermentation; after stirred, the fermented fish paste is set to breathe freely for 10~120 seconds;
   (6) cooking fish sauce: the fish paste obtained in step (4) is steamed in a steamer for 20~40 minutes until the fish paste is thoroughly cooked;
   (7) sterilization of fish paste: the cooked fish paste in step (6) is filled into cans, sealed, and sterilized for 15~20 min at 120° C.; the fermented fish paste products are obtained.

* * * * *